United States Patent
Baloch et al.

(10) Patent No.: US 9,622,820 B2
(45) Date of Patent: Apr. 18, 2017

(54) FEATURE-DRIVEN RULE-BASED FRAMEWORK FOR ORTHOPEDIC SURGICAL PLANNING

(71) Applicants: Sajjad Hussain Baloch, Monmouth Junction, NJ (US); Suraj Ravi Musuvathy, Lawrence, NJ (US); Guanglei Xiong, Plainsboro, NJ (US); Lawrence Spivey, Channahon, IL (US); James B. Thompson, St. Charles, IL (US); Tong Fang, Morganville, NJ (US)

(72) Inventors: Sajjad Hussain Baloch, Monmouth Junction, NJ (US); Suraj Ravi Musuvathy, Lawrence, NJ (US); Guanglei Xiong, Plainsboro, NJ (US); Lawrence Spivey, Channahon, IL (US); James B. Thompson, St. Charles, IL (US); Tong Fang, Morganville, NJ (US)

(73) Assignee: Siemens Product Lifecycle Management Software Inc., Plano, TX (US)

(*) Notice: Subject to any disclaimer, the term of this patent is extended or adjusted under 35 U.S.C. 154(b) by 545 days.

(21) Appl. No.: 13/871,675

(22) Filed: Apr. 26, 2013

(65) Prior Publication Data
US 2013/0297265 A1 Nov. 7, 2013

Related U.S. Application Data

(60) Provisional application No. 61/642,065, filed on May 3, 2012.

(51) Int. Cl.
A61B 34/10 (2016.01)
A61B 19/00 (2006.01)
G05B 17/00 (2006.01)
G06F 19/00 (2011.01)
G06F 17/50 (2006.01)
G06T 19/00 (2011.01)

(52) U.S. Cl.
CPC .............. *A61B 19/50* (2013.01); *A61B 34/10* (2016.02); *G05B 17/00* (2013.01);
(Continued)

(58) Field of Classification Search
None
See application file for complete search history.

(56) References Cited

U.S. PATENT DOCUMENTS 4,936,862 A * 6/1990 Walker ................ A61F 2/30942
128/898
6,711,432 B1 * 3/2004 Krause ................... A61B 17/15
128/922

(Continued)

FOREIGN PATENT DOCUMENTS

CN 101627411 A 1/2010
CN 101815477 A 8/2010
WO 2009025783 A1 2/2009

OTHER PUBLICATIONS

International Search Report and Written Opinion dated Sep. 20, 2013 for corresponding PCT Patent Application No. PCT/US2013/038607.

(Continued)

*Primary Examiner* — Kibrom K Gebresilassie

(57) ABSTRACT

The design process for the surgical plan in orthopedics and/or the design of a personalized cutting guide and/or implant are automated in a workflow frame work. Abstracted rules are scripted through a sequence of operations to alter a bone surface or model for fitting an implant. Using bone information for a specific patient, the proper implant and series of cuts are determined using the rules. A corresponding cutting guide may be fitted to the bone information for the specific patient. Surgical planning of bone replacement implants is performed automatically.

18 Claims, 3 Drawing Sheets

(52) U.S. Cl.
CPC ... *A61B 2034/102* (2016.02); *A61B 2034/105* (2016.02); *A61B 2034/108* (2016.02); *G06F 17/50* (2013.01); *G06F 19/3437* (2013.01); *G06T 19/00* (2013.01)

(56) References Cited

U.S. PATENT DOCUMENTS

| | | | | |
|---|---|---|---|---|
| 7,447,556 | B2* | 11/2008 | McBagonluri | H04R 25/552 381/312 |
| 8,332,061 | B2* | 12/2012 | Baloch | G06F 17/50 700/182 |
| 8,847,952 | B2* | 9/2014 | Takashima | G06T 17/20 345/420 |
| 9,119,722 | B1* | 9/2015 | Kusuma | A61F 2/36 |
| 9,208,558 | B2* | 12/2015 | Dean | G06T 7/0012 |
| 2002/0007294 | A1 | 1/2002 | Bradbury et al. | |
| 2002/0186818 | A1 | 12/2002 | Arnaud et al. | |
| 2003/0015208 | A1* | 1/2003 | Lang | A61B 6/505 600/562 |
| 2004/0068187 | A1* | 4/2004 | Krause | A61B 17/15 600/443 |
| 2004/0101179 | A1* | 5/2004 | Suryanarayanan | G06T 7/0012 382/128 |
| 2007/0189564 | A1* | 8/2007 | McBagonluri | H04R 25/552 381/322 |
| 2008/0161815 | A1 | 7/2008 | Schoenefeld et al. | |
| 2009/0264894 | A1* | 10/2009 | Wasielewski | A61B 19/46 606/102 |
| 2010/0076563 | A1* | 3/2010 | Otto | A61B 5/103 623/20.14 |
| 2010/0094446 | A1* | 4/2010 | Baloch | G06F 17/50 700/98 |
| 2010/0292963 | A1* | 11/2010 | Schroeder | A61F 2/30 703/1 |
| 2011/0087465 | A1 | 4/2011 | Mahfouz | |
| 2011/0092804 | A1 | 4/2011 | Schoenefeld et al. | |
| 2013/0292870 | A1* | 11/2013 | Roger | A61B 17/155 264/138 |
| 2013/0332128 | A1* | 12/2013 | Miles | A61B 19/50 703/6 |
| 2014/0244220 | A1* | 8/2014 | McKinnon | A61B 19/50 703/1 |
| 2014/0371896 | A1* | 12/2014 | Landon | B29C 67/0077 700/98 |
| 2015/0245879 | A1* | 9/2015 | Nikou | A61B 19/50 606/88 |
| 2015/0347710 | A1* | 12/2015 | Couture | A61B 34/10 700/98 |

OTHER PUBLICATIONS

R. L. Dooley et al., "Orthopedic Implant Design, Analysis, and Manufacturing System," In: Proceedings of the Symposium on the Engineering of Computer-Based Medical Systems, pp. 60-64, 1988.

M. E. Riechmann et al., "Computer-Aided Design and Computer-Aided Manufacturing of Below-Knee Prosthetics," In: Proceedings of the IEEE Seventeenth Annual Northeast Bioengineering Conference, pp. 154-155, 1991.

P. Hammond et al., "A Logic-Based Model of Prosthesis Design," In: IEE Colloquium on Intelligent Design Systems, pp. 4:1-3, 1997.

D. Zhu et al., "Customized Design and Fabrication of Permanent Dental Restoration," In: BMEI 2009—$2^{nd}$ International Conference on Biomedical Engineering and Informatics, pp. 1-4, 2009.

J. R. Strub et al., "Computer-Aided Design and Fabrication of Dental Restorations Current Systems and Future Possibilities," The Journal of the American Dental Association, vol. 137(9), pp. 1289-1296, 2006.

X. Ye et al., "Reverse Innovative Design—An Integrated Product Design Methodology," Computer-Aided Design, vol. 40(7), pp. 812-827, 2008.

R. Paulsen et al., "Building and Testing a Statistical Shape Model of the Human Ear Canal," In MICCAI 2002—Medical Image Computing and Computer-Assisted Intervention—Part II, pp. 373-380, 2002.

R. Paulsen et al., "Shape Modelling Using Markov Random Field Restoration of Point Correspondences," In IMPI 2003—Information Processing in Medical Imaging, pp. 1-12, 2003.

R. Paulsen, "Statistical Shape Analysis of the Human Ear Canal with Application to In-the-Ear Hearing Aid Design," Ph.D. thesis, Informatics and Mathematical Modelling, Technical University of Denmark, 2004.

S. Darkner et al., "Analysis of Deformation of the Human Ear and Canal Caused by Mandibular Movement," In: MICCAI 2007—Medical Image Computing and Computer-Assisted Intervention, pp. 801-808, 2007.

G. Unal et al., "Customized Design of Hearing Aids Using Statistical Shape Learning," In: MICCAI 2008—Medical Image Computing and Computer-Assisted Intervention—Part I, pp. 518-526, 2008.

Siemens PLM: NX CAD, http://www.plm.automation.siemens.com/en.us/products/nx., Webpage, pp. 1-4, Apr. 23, 2013.

Dassault Systemes, CATIA, http://www.3ds.com/products/catia., Webpage, pp. 1-2, Apr. 23, 2013.

K. Sickel et al., "Towards Automation in Hearing Aid Design," Computer Aided-Design, vol. 43(12), pp. 1793-1802, 2011.

C. Donnelly et al., "The Bison Manual, Using the YACC Compatible Parser Generator," pp. 1-210, Dec. 12, 2012.

G. Henry, "Gray's Anatomy," Descriptive and Surgical (1858), Webpage, p. 1, Apr. 23, 2013.

D. Liu et al., "Search Strategies for Multiple Landmark Detection by Submodular Maximization," IEEE Conference on Computer Vision and Pattern Recognition, pp. 1-8, 2010.

G. Xiong et al., "Automatic Feature Detection for Implant Design in Knee Replacement Surgery," Technical Report, Siemens Corporate Research, 2012.

CN Office Action dated Oct. 25, 2016, for CN Application No. 201380022856.2, 10 pages.

\* cited by examiner

FEATURE-DRIVEN RULE-BASED FRAMEWORK FOR ORTHOPEDIC SURGICAL PLANNING

RELATED APPLICATIONS

The present patent document claims the benefit of the filing date under 35 U.S.C. §119(e) of Provisional U.S. Patent Application Ser. No. 61/642,065, filed May 3, 2012, which is hereby incorporated by reference.

TECHNICAL FIELD

This disclosure relates in general to the field of orthopedic surgical planning, and, more particularly, to automatic planning assistance.

BACKGROUND

During orthopedic surgery, a surgeon trims a pathological part of the bone and replaces the pathological part with an implant. Two major factors influence the eventual outcome of a bone surgery—the ability of a surgeon to accurately remove the pathological bone segment while keeping the healthy bone intact and the ability of the surgeon to replace the pathological bone segment with an optimally matched implant. For performing the surgery with minimal incision, the bone is trimmed with the aid of a patient specific cutting guide. The guide contains one or more saw-slots and some landmarks for accurately performing the reference cuts. In the surgical planning phase, the personalized cutting guide is designed, and a surgical plan that exploits the reference cuts and any other cuts to define optimal placement of a surgical implant is created by the surgeon and a designer. The plan then guides a surgeon in placement of the implant after performing the initial cuts on the bone.

The design of the patient specific cutting guide and the construction of the surgical plan are carried out in the planning phase by experienced designers. For this purpose, the designers follow a set of operations defined in pre-approved work instructions. In most cases, the surgical planning procedure is pre-approved by a regulatory body, and the designers have to strictly follow the rules specified in the approved procedure. To this end, the designers of the cutting guide rely on interactive, yet-manual, 3D modeling software to create the cutting guide. However, this manual design process results in increased design time, lack of repeatability, reduced consistency, and a potential for unintentional deviation from the pre-approved procedure.

SUMMARY

By way of introduction, the preferred embodiments described below include methods, systems, instructions, and computer readable media for orthopedic surgical planning. The design process for the orthopedic surgical plan and/or the design of a personalized cutting guide are automated in a workflow framework. Abstracted rules are scripted through a sequence of operations to alter a bone surface or model for fitting an implant. Using bone information for a specific patient, the proper implant and series of cuts are determined using the rules. A corresponding cutting guide may be fitted to the bone information for the specific patient. Surgical planning of bone replacement implantation is performed automatically.

In a first aspect, a method is provided for orthopedic surgical planning. A knowledgebase of rules for orthopedic surgery to a surface is provided. The surface representing a bone, implant, or cutting guide is obtained. A processor selects a first rule of the knowledgebase, identifies at least one anatomical feature for the first rule, detects at least one anatomical feature of the surface, defines an alteration to the surface as a function of the first rule and at least one anatomical feature, alters the surface according to the alteration, resulting in a first altered surface, and outputs a reference plan indicating an implant with reference to the first altered surface. The processor also generates a cutting guide model as a function of the first altered surface. The cutting guide model indicates a cut position on the bone relative to the first altered surface.

In a second aspect, a non-transitory computer readable storage medium has stored therein data representing instructions executable by a programmed processor for orthopedic surgical planning. The storage medium includes instructions for sequencing through work instructions representing alterations of geometry based on anatomical features, generating an orthopedic surgical plan for a patient in response to the sequencing, modeling implant placement relative to bone of the patient, and designing a cutting guide for the bone of the patient.

In a third aspect, a non-transitory computer readable storage medium has stored therein data representing instructions executable by a programmed processor for orthopedic surgical planning. The storage medium includes instructions for automatically creating a surgical plan of alterations specific to a patient for implanting in a bone of the patient, and automatically designing a cutting guide for the alterations, the cutting guide specific to the patient.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DESCRIPTION OF EXEMPLARY EMBODIMENTS

A feature driven rule-based framework automates orthopedic surgical planning. A 3D modeling framework automatically creates a cutting guide and a surgical plan. The patient bone geometry and a set of anatomical features defined relative to the bone are combined with process specific work instructions. The work instructions represent processing for the specific surgery. The work instructions are abstracted with expert knowledge into feature dependent machine interpretable rules in a knowledgebase. A set of anatomical features are then employed by a shape modeler to determine concrete implant placement and cutting guide design operations. These operations are performed sequentially to carry out the implant planning. By a priori defining an entire surgical planning workflow through a scripting language, thereby yielding flexible and customizable automation via scriptable rules, versatility is provided for implementation with different orthopedic surgeries. Tedious manual intervention may be reduced or eliminated while providing precision and reproducibility. Adherence to a pre-approved, regulatory workflow may be more likely.

Orthopedic surgical planning involves the automatic design of a personalized cutting guide and a surgical plan specific to a patient. The abstract rules derived from the actual work instruction manual are encoded. Using the rules, the system automatically detects features and landmarks on a model of the bones of the specific patient. The detected features and landmarks are combined with the abstract rules to define concrete implant placement operations, virtual bone cutting planes, a surgical plan, and a cutting guide or guides personalized for the given patient. The surgical plan shows how to perform cuts and how to use the cutting guide and implants for the patient.

The feature-driven personalization is automatic, repeatable, and consistent with this workflow automation. The surgeon, designer, manufacturer, or other planner may benefit from automated planning due to reduction in planning time and/or more reliable guide design. The patient may benefit by more accurate cutting and implant placement. The manufacturer of the implant may benefit by more accurate determination of the proper implant to use. The manufacturer of the cutting guide may benefit by more accurate and specific design. An automatic design solution is provided to any one or more users, providing repeatability and consistency of designs as well as reduced times. A platform for the digitization of the work instructions allows a user to implement the entire surgical planning and cutting guide design process in the form of a machine interpretable script of work instructions.

Figure 1:
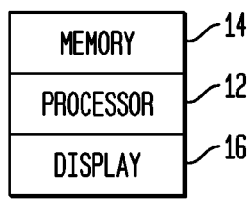
FIG. 1 is a simplified block diagram of a system for automated orthopedic surgical planning.

FIG. 1 illustrates an exemplary system or platform for automated orthopedic surgery planning. The system as shown represents a computer, laptop, tablet, workstation, server, or other processing device. A surgeon, manufacturer, designer, or other user operates the system for automated planning and/or cutting guide design. In alternative embodiments, the system is part of a network allowing a client-server arrangement where the client requests planning or design, and a server or servers provide the automated planning or design functionality.

The system includes a processor 12, a memory 14, and a display 16. Additional, different, or fewer components may be provided. For example, a user input, network interface, and/or multiple processors are provided.

The display 16 is a CRT, LCD, flat panel, plasma, projector, printer, combinations thereof or any other now known or later developed display. Using a graphics processing unit or other hardware or software, the display 16 generates black and white or color pixels in a Cartesian or other coordinate format for presenting a graphical user interface, surgical plan, implant model, implant image, cutting guide model, cutting guide image, bone image, or combinations thereof. In alternative or additional embodiments, the plan and/or models are output to the memory 14, a different memory, or transmitted over a network.

The memory 14 stores data, such as a knowledgebase, rules, script, model parameters, other model information, feature detectors, medical image data (e.g., segmented bone information), bone model, implant model, cutting guide model, computer assisted design (CAD) tools, or other information use for orthopedic surgical planning and cutting guide design. Other data may be stored.

Alternatively or additionally, the memory 14 is a non-transitory computer readable storage medium storing data representing instructions executable by the programmed processor for automated orthopedic surgical planning. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 12 is a general processor, applications specific integrated circuit, digital signal processor, field programmable gate array, multiple processors, analog circuit, digital circuit, network server, graphics processing unit, combinations thereof, or other now known or later developed device for performing automated workflow. The user may input an activation command, select a patient, select patient bone data, select a surgical procedure or otherwise initialize the workflow, but the processor 12 sequences through the rules and generates the surgical plan and/or cutting guide design without further user input. In alternative embodiments, the user may confirm and/or alter operation of the workflow at different points during the workflow.

The processor 12 uses abstracted work instructions and expert knowledge for automated workflow. The work instructions and knowledge are stored as feature-dependent machine interpretable rules in a knowledgebase. Once the design rules have been implemented and fed into the system, the processor 12 sequentially executes the rules for a given surgery and automatically determines the design and/or planning operations using anatomically aware CAD tools.

Anatomical awareness is incorporated through built-in feature detection. The processor 12 implements a shape modeler with a set of anatomical features to determine concrete implant placement and cutting guide design operations. Given a new patient anatomy (i.e., a bone shape specific to a patient) in the form of geometric data, the processor 12 processes the script. The script utilizes anatomical features to uniquely determine how to carry out the plan and cutting guide design. The representative features for a given bone geometry are detected and utilized to define various measurements for the selection and the placement of the implants and/or cuts.

The processor 12 may automatically find the optimal size of the implant for the best fit and the optimal placement on a bone for best alignment of the bone segments or the joints. By processing through the rules sequentially, implant planning is performed. By defining an entire surgical planning workflow through a scripting language, tedious manual intervention may be limited or avoided. The workflow provides design for the implant and/or cutting guide. More than modeling these tools, the processor 12 also provides a surgical plan, which serves as a guide to the surgeon on how to practically carry out the surgery. The rules may provide for planning with respect to adjacent bones in a dependent manner. Multiple implants may be added, so the rules deal with multiple bones adjacent to each other.

Figure 2:
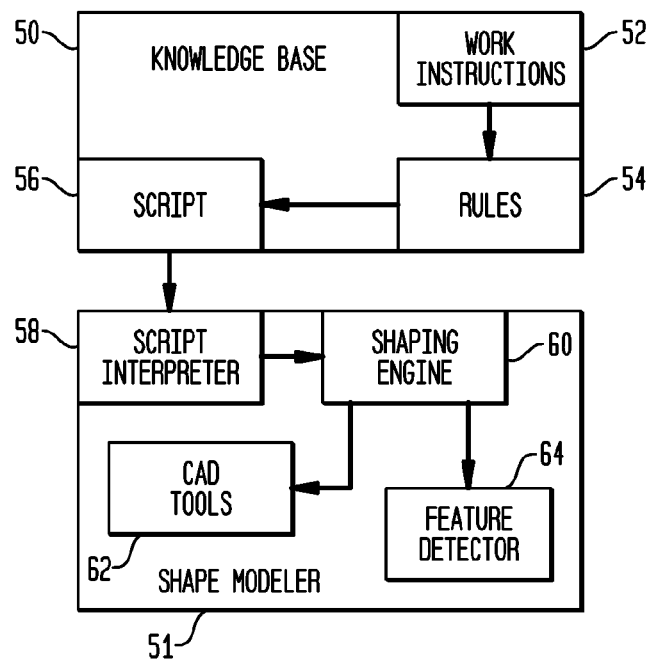
FIG. 2 illustrates a schema for automated orthopedic surgical planning, according to an embodiment.

FIG. 2 shows a representation of the workflow and corresponding processing engines implemented by the processor 12. The workflow includes a knowledgebase 50 and a shape modeler 51. The knowledgebase 50 includes work instructions 52, rules 54, and script 56. The shape modeler 51 includes a script interpreter 58, a shaping engine 60, CAD tools 62, and feature detectors 64. Additional, different, or fewer components may be provided.

The knowledgebase 50 represents information about the surgical procedure. The work instructions 52 may be considered part of the knowledgebase or may be conceptual information that is included in the knowledgebase data as the rules 54. Similarly, the rules 54 may not be included in the knowledgebase other than through use in creating the script 56 for use by the shape modeler 51.

The shaping engine 60 may include the script interpreter 58 rather than being separate. Only one, two, or more different feature detectors 64 may be used. The feature detectors 64 are detection applications or refer to applications provided in one or more separate systems, such as on a picture achieving and communications system (PACS) or a medical imaging system. Similarly, any number of CAD tools 62 may be incorporated. The CAD tools 62 include CAD applications or are references to CAD applications provided in a separate system.

Manually, the design of a cutting guide and a surgical plan is a step-wise process defined in the process work instructions. In the approach of FIG. 2, the process is automated through a modeling framework. The descriptive work instructions are translated into machine interpretable scriptable rules. The rules are defined in the script 56 specified in the knowledgebase 50. The workflow system is pre-loaded with the script 56 and/or rules 54 to implement the workflow. The implementation/design of the script is done offline and is fixed once approved by the regulatory body. For a patient during surgical planning, the scripts 56 are fed into the system through the script interpreter 58, which in turn is embedded in or feeds information to the shape modeler 51.

The shape modeler 51 designs a surface or shape using the CAD tools 62, which are invoked automatically as directed by the scripts 56. The surface shaping engine 60 interacts with the script interpreter 58 to sequentially feed the shaping engine 60 with rules from a digitized workflow. Each rule r is translated to an operation $T_i^F(r)$ that is defined by features. The feature detectors 64 are invoked to determine the locations relative to the bone to implement the operation for changing the bone, implant, and/or cutting guide with the CAD tools 62 corresponding to the surgery work instructions 52. Sequential execution of the script 56 is ensured through the script interpreter 58, which parses the rules 54 and maintains the state of the current rule in the digitized workflow.

The workflow is used for any orthopedic surgery. The surgery may be for removal of bone without an implant. For example, the workflow provides a plan and a cutting guide design without an implant. The surgery may be for a plan without a cutting guide design. The surgery may be for designing an implant without a cutting guide or without removal of bone. The workflow may be used to select a type (e.g., style) and/or size of implant to use. The surgery may involve alterations to only one bone or alterations to connected or adjacent bones. Connection being used to indicate interoperability or being part of a common joint.

Any bone or bones may be involved. For illustration purposes, the framework is explained for total knee replacement implants and corresponding surgery. The workflow may be used for other surgeries or for other bones by conforming the knowledgebase and feature detectors to the surgery or bone.

During a total knee replacement surgery, a surgeon trims the bone using cuts, such as three different planar cuts A, B, and C. Subsequently, the surgeon replaces the removed part of the bone with an implant of the correct type and size. Typically, both tibia and femur implants are inserted at the same time. The accuracy of the reference cuts is important for the recovery of a patient, as the cuts determine the alignment of the bones as well as the stresses on the walls of the bone. For example, if cut A is too deep, the leg may become too short. If the orientation is off, then the femur implant may not align well with the tibia implant. Similarly, incorrect location and alignment of cuts B and C may remove extra bony material and may result in an increased amount of stress, thereby increasing the risk of fracture. For this reason, a customized cutting guide is designed and manufactured. The surgeon uses the patient personalized cutting guide to assist in accurately placing the reference cuts. The cutting guide indicates the position of the cut for one, two, or more of the cuts to be performed. For example, the cutting guide indicates the position for cut A, where cuts B and C are defined thereby so not separately guided by the cutting guide. The cutting guide may alternatively include edges, slots, or printing indicating the relative position of cuts B and C to the cut A.

The number of cuts depends on the construction of the implants and the bone. The orientation and location of the implants are largely determined by the anatomy of a patient. In this regard, anatomical features play an important role. Accurate detection of such features on the patient bones provides for correct implant selection and placement. Various anatomical features of interests may be considered, depending on the implant, the bone, and the surgical process. In the context of knee implants, some anatomical features used are the axis of the femur and the most distal point of the femur. These features are automatically detected on the patient bone. The workflow framework automatically generates the surgical plan for a surgeon, where relative measurements with respect to the anatomical features are provided to ensure accurate cuts as well as implant placement. The selection of the features is application specific and is determined by the corresponding work instructions 52. The workflow framework is independent of the choice of the underlying feature detection algorithms. Any algorithms for detection may be used.

Figure 3:
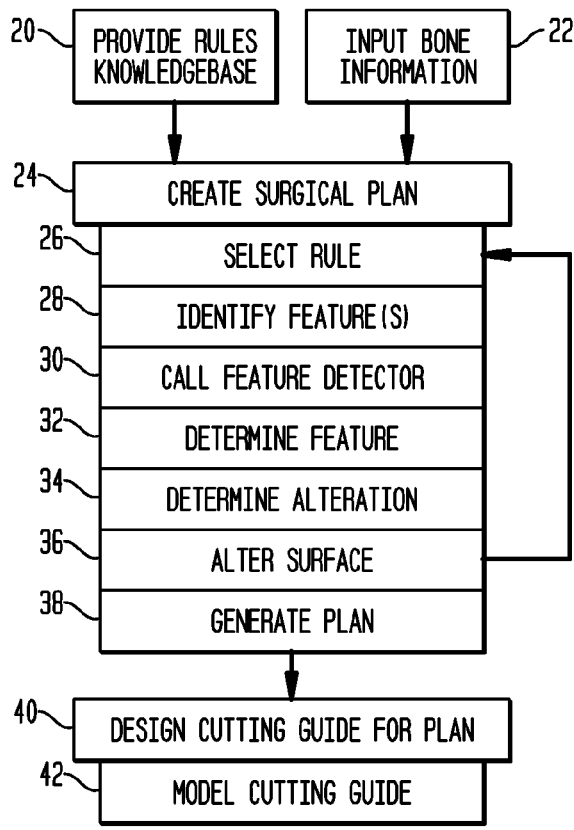
FIG. 3 is a flowchart diagram of one embodiment of a method for automated orthopedic surgical planning.

FIG. 3 shows a method for automatic orthopedic surgical planning. The method is implemented using the system of FIG. 1, a processor, a server, a computer, the workflow system of FIG. 2, and/or a different system. In general, a processor receives input including type of surgery, a knowledgebase for the surgery, any feature detectors, any CAD tools, and a representation of the patient's bone. The processor performs the method to output a surgical plan, an implant design, and/or a cutting guide design.

Additional, different or fewer acts may be provided than shown in FIG. 3. For example, acts for accessing other types of data, acts for transmitting an output, and/or acts for storing the models or plans are provided.

The acts are performed in the order shown or different orders. For example, the provisioning of the rules and the patient specific bone information in acts 20 and 22 are performed in any order or simultaneously. Acts 26-38 represent example acts for implementing act 24, so performance of any of acts 26-38 may be considered as part of performing act 24. Alternatively, act 24 may be considered to have been performed once the last act (e.g., 38) is performed. Act 42 represents an example act for implement act 40, so performance of act 42 may be performance of act 40.

Figure 4:
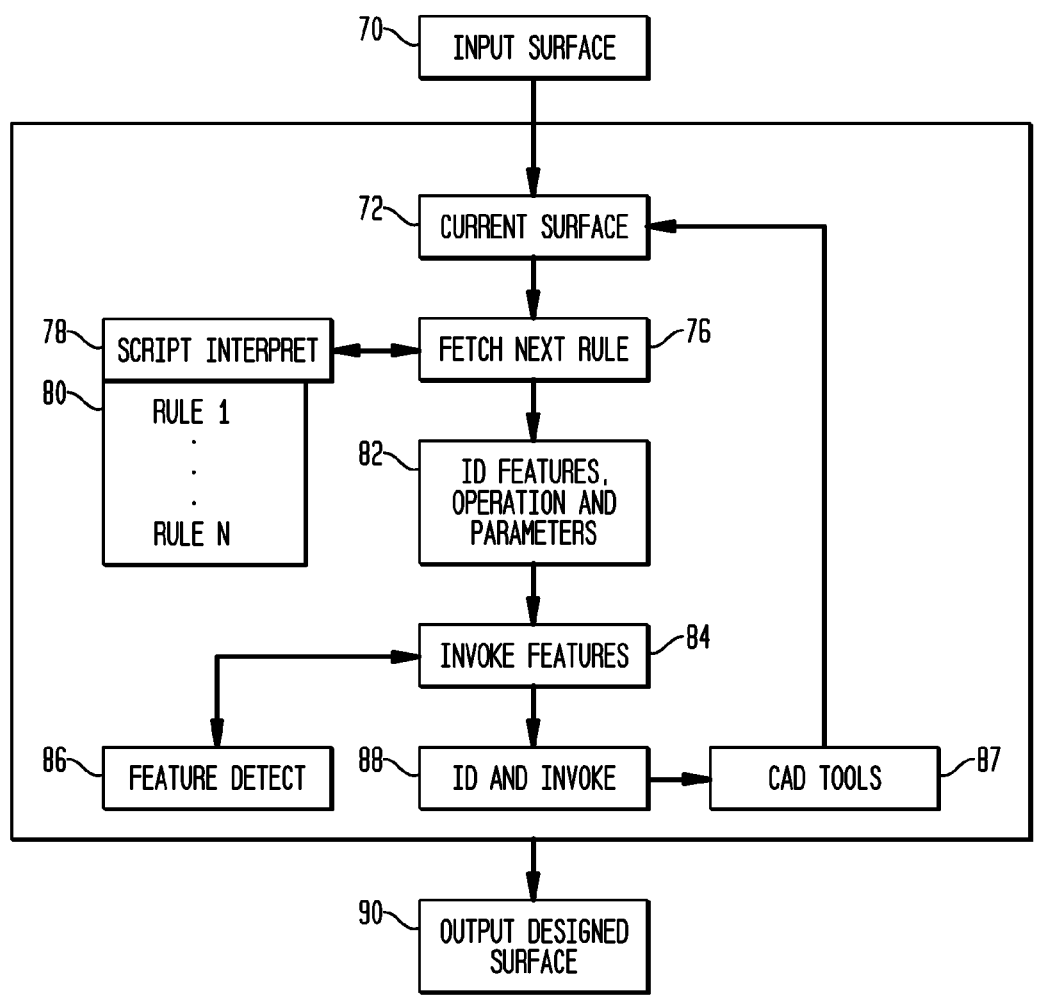
FIG. 4 is a flowchart diagram of an embodiment of a method for generating an orthopedic surgical plan.

FIG. 4 shows another embodiment of a method for automatic orthopedic surgical planning. The method of FIG. 4 corresponds to the implementation of the shape modeler 51. The acts of FIG. 4 are implemented by a same or different system than the acts of FIG. 3. The same system may implement a combination of some or all of the acts of FIGS. 3 and 4 in a given application to generate a surgical plan, implant model, and/or cutting guide model. Alternatively, FIGS. 3 and 4 represent alternative example embodiments.

Orthopedic surgical planning for joint replacement implants includes determining optimal size of implants, position of the implants, reference cuts to remove pathological bone regions, and/or customization of cutting guides for performing initial, one, multiple, or all alteration of the bone or bones. The planning is implemented in a 3D modeling framework that automatically creates cutting guides and surgical plans. Human readable work instructions are translated to machine interpretable rules in the proposed framework. Rules are specified through a scripting language and are based on the features detected on a bone surface or relative to the bone specific to a patient. Flexibility of this approach lies in the diversity of rules, which allows handling various configurations in digital manufacturing and planning.

In act 20 of FIG. 3, a knowledgebase of rules for orthopedic surgery to a bone is provided. The knowledgebase is data. The data include the rules or script representing the rules. The expert knowledge about the cuts to be made, the position of the cuts relative to features of the bone, the order of the cuts, the size of the implant, the placement of the implant relative to other bone, and/or other considerations for planning are incorporated into the knowledgebase.

The rules are context free grammar expressed in a scripting language supporting geometric primitives. Other implementations may be provided, such as using scripts specific to a surgery or reliant on context.

The role of the knowledgebase is to digitally represent a workflow through the set of rules R derived from the work instructions. The rules are application specific and address realizations of the class of surfaces. The rules describe how to perform various steps and which features to utilize in performing each step. A step, in turn, indicates one or more surface modifications for the patients bone, such as a step for cutting along cut A, another step for cutting along cut B, and a step for cutting along cut C.

The rule indicates adjustment or positioning operations $T_i^F(r)$ and features F used for performing the operations. For example, for cutting a bone surface, the knowledgebase specifies a rule r that defines where to perform a cut consistently for a wide range of surfaces. Following the rule computes the cutting plane as well as the type of cut. Although surfaces may exhibit variability, their class membership ensures that some canonical set of features F is identifiable and is sufficient to define such a plane. The existence of the features detected in the patient bone model drives the framework. The knowledgebase implements the rules in a scripting language, allowing complete flexibility for various implant and guide types and target shapes.

The rules knowledgebase may include scripting of rules associated with more than one bone. For example, two implants are aligned relative to the tibia and femur as well as each other. The orientation of the bones to each other may also indicate relative positioning of the implants. The relative position of the implants dictates the bone shaping to occur, such as the position of one or more cuts. The rules incorporate the relationships between implants and/or bones, such as through detection of features on multiple bones to determine a cut location on one of the bones. Alternatively, one, more, or all rules are for one bone based only on one bone.

In act 22 of FIG. 3 and act 70 of FIG. 4, patient specific bone information is obtained. The user inputs the bone information by selecting a dataset, image, or images for a patient. The information may be obtained by receiving a transmission, uploading from memory, or scanning the patient.

The bone information is a dataset representing a volume of the patient. For example, a computed tomography (CT) or magnetic resonance (MR) dataset represents a volume including the joint. Data from other imaging modalities may be used. The data within the dataset represents a surface of the bone as well as other structures. Alternatively, bone-segmented information is obtained. The locations representing the bone and/or the surface of the bone are segmented and the segmented information is received without data representing other structures. Data for one or more other structures may be included with the bone segmented information. Any segmentation may be used.

The bone information represents an organic shape. Different patients have different size, shape, density, or other bone characteristics. The obtained bone information indicates one or more of these characteristics for a particular patient.

In act 24, a surgical plan is automatically created from the rules knowledgebase and the bone information. The surgical plan indicates one or more steps to be performed by the surgeon for implanting in a bone of the patient. The surgical plan may include instructions or actions to be performed (e.g., cut at location x), one or more images (e.g., showing where to cut or position and a final result), one or more characteristics of the implant (e.g., size, type, and/or shape), and/or other information for the surgeon. For example, the surgical plan shows one or more views of the patient bone with overlaid lines or graphics indicating cutting locations, directions, and corresponding features (see FIG. 5).

FIG. 3 shows creation of the surgical plan as including acts 26-38. The acts are provided in the context of outputting a plan. FIG. 4 shows creation of the surgical plan as acts 72-88. The acts are provided in the context of outputting an image representing the plan and/or of the bone after implementing the plan. Additional, different, or fewer acts may be used. In one embodiment, a simplified surgical planning workflow includes detection of anatomical features, determination of the rough size of an implant, optimal placement and size adjustment of the implant, creation of a reference plan for a surgeon indicating implant size, type, and placement with respect to various features, and inclusion of reference cuts in the surgical plan. In more complex workflows, personalized implants may also be designed.

The surgical plan may be created by one pass through the acts. FIGS. 3 and 4 both show repetition for sequencing through the set of rules in the knowledgebase. The repetition occurs until the rules in the script are performed. The work instructions are incorporated in the rules and corresponding script in an order of operation. The workflow for surgical planning and cutting guide design includes a sequence of steps specified in work instruction manuals for the designers. Each pass through includes selecting the next rule, identifying corresponding features, defining an alteration, and altering the bone representation. Each pass through implements the operation or operations of the next rule in the sequence. The rules of the sequence represent different or a sequence of alterations of the bone geometry. One or more rules may alternatively or additionally represent other actions than bone geometry alteration. The process is repeated until the script interpreter is exhausted of all applicable rules, and the current surface is outputted as the designed or desired shape of the bone and/or the cutting guide for the desired bone shape.

The use of a collection of rules and corresponding script in the knowledgebase with the workflow sequencing is modular. The same structure and approach may be used for different orthopedic surgeries. The rule set in the knowledgebase may change, but the workflow and automated processing is the same or similar. The advantage of this modular approach is that the workflow modeler and the shape engine are automated and not specific to a particular application. By modifying the scriptable rules and the associated feature set, the application may be changed.

The scripting allows configuration of the approach. The sequencing is implemented by the script interpreter. The script interpreter or a controlling application interprets script for the work instructions of the knowledgebase. To implement the workflow automatically, the script interpreter interprets the rules in the order indicated by the knowledgebase.

The sequencing occurs automatically. Once activated, the surgical plan is created without user input or interaction. In other embodiments, the user is prompted to confirm one, more, or all operations. For example, the proposed result of the rule implementation is presented for the user. The user then confirms proper operation and/or makes an alteration.

In act 72 of FIG. 4, a current surface is determined. Where the sequence is in the first pass through, the current surface is the input surface from act 70. For subsequent passes, the current surface is the input surface with one or more alterations incorporated. A given rule may define an alteration to the surface, so the current surface after that alteration includes the alteration.

In act 76 of FIG. 4 and act 26 of FIG. 3, a rule is selected. The rule is selected from the knowledgebase 80. By sequencing through the rules, the different rules are selected as part of the sequence. In act 78, the script interpreter accesses the script in an order defined in the knowledgebase. For example, the rules are provided or addressed in order from a first rule through to a last rule. One or more rules may be included multiple times in the sequence. As the alterations or other operations of the rule are implemented in the creation of the plan, the script interpreter is requested or automatically selects the next rule.

For realizing the rules with the script interpreter, a scripting language with context free grammar is designed. For example, Bison and Flex tools are used. The language supports standard data types, in addition to geometric primitives such as points, planes, and matrices (e.g., defining location or orientation in three dimensions), which allows manipulation of surface meshes. The scripting language may include control structures, such as IT-THEN-ELSE, and FOR and WHILE loops. Any programming structures may be used. Specialized functions may include interfaces to CAD tool application programming interfaces (API), Feature Detection API functions, and primitive surface manipulators. A customized language may allow simple handling of the scripts and easy integration with a CAD application, while keeping the CAD application flexible. In other embodiments, a standard or generic programming language is used.

In acts 28 and 82, one or more anatomical features are identified. The rule may be based on one or more anatomical features, so the rule indicates the features. The script interpreter identifies the features to be used for implementing the rule. The features are used to define a surface modification or position operation. In one example, the rule defines cut A as a cut on the bone at a distance x from the femoral head with the normal n. The number of cuts depends on the construction of the implants. Their orientation and location are largely determined by the anatomy of a patient. In this regard, anatomical features are utilized to determine each surface modification or positioning operation. To this end, various anatomical features are identified by the rules.

The scriptable rules may be related to one or more features. In general, different configurations or types of implants employ different combinations of features. The implants may be seated differently, so need different alterations of the bone. A given alteration may be with reference to the same or different feature set of the bone than other alterations. The combination of features is selected through IF-THEN-ELSE statements in the script. For example, the rules include, as self descriptive, CutFemurBoneAtPlane, PartitionFemurCartilage, and CutTibiaAtPlane. The rules reference the location of the cuts and/or partitions. In an example, the femur cutting plane A is determined from two features. The implant is to rest on this plane, and other cutting planes are defined with reference to this plane. In this example, the plane is placed at a distance x from the most distal point on the femur. The most distal point is a feature of the bone surface. The plane normal is aligned with the anatomical axis of the femur. The anatomical axis is a feature of the bone surface. The script may be represented as:

```
//Detect anatomical axis
anatomicalaxis=DetectFemurAnatomicalAxis
//Detect most distal point
mostDistalPoint=DetectFemurMostDistalPoint
//Move distal point in the superior direction
shiftedMostDistalPoint=
mostDistalPoint-x*anatomicalAxisDirection
//Define the cutting plane
cuttingPlane=Plane(shiftedMostDistalPoint,
anatomicalAxisDirection)
```

Other script may be used. The script indicates the operation to be performed, the features to use for the operation, and the parameters (e.g., distance, angle . . . ) for the operation. Additional, different, or less information may be indicated.

In act 30 of FIG. 3 and act 84 of FIG. 4, one or more feature detectors are called. The feature detector is invoked to detect the feature. The feature detector is a separate application or is included as part of the workflow. For example, feature detectors are implemented by the same processor but are separate executable files. The script interpreter calls the feature detectors to cause detection of the feature identified in the rule. The feature detector itself is or is not within the script interpreter.

Any feature detector may be used. The feature detectors locate the feature on the bone surface or relative to the bone. The input bone surface or the current bone surface is used by the feature detectors. Other information may be alternatively or additionally used, such as other data representing the patient. Using filtering, image processing, machine-learnt classifiers, or other detection, the data is processed to locate one or more features of the bone of the patient.

In acts 32 and 86, the called feature detector detects one or more anatomical features. The invoked feature detector is activated and runs. The detected feature is on the bone surface, but may be within the bone or spaced from the bone. Any parameter or parameters representing the feature are output for use in the workflow. For example, a point, line, surface, plane, volume, or combinations thereof are output. The locations are relative to the bone surface, either the input or the current bone surface.

In act 34, the alteration associated with the features is determined. Features are used to uniquely define the actual surface modification operation. The alteration to be performed is determined with the detected features and based on the operation defined by the rule. The features indicate the locations for removal or alteration of the pathological bone. When initialized with a given bone surface, the surface shape engine queries the rules from the script interpreter, and executes the instruction indicating the alteration relative to the detected feature. The features are detected on the fly, and the surface modification operation is determined at the run-time. The cut position to remove the bone is located and/or the portion of the bone to be removed relative to the cut position is indicated. The location of a drill hole and depth or other information may be determined as the alteration.

The alteration is for a smoothing, scooping, flattening, drilling, cutting, removing, shaving, or other change to the bone through surgery or the cutting guide or implant during design. The alteration may be to add, such as adding a fixture, layer of glue, or other substance. In an example for local scooping or smoothing, the knowledgebase informs the surface shape engine about the operation (i.e., scooping or smoothing), the scooping or smoothing parameters, and the identifier (e.g., feature) for the corresponding region of interest or alteration location. Based on this identifier, the area to be scooped or smoother is determined. Based on other parameters, the extent of scooping or smoothing is determined.

In act 36, the surface is altered based on the alteration. The surface being altered is the representation of the bone surface. The surface shaping engine alters the virtual surface represented by data. Removal of bone and/or addition is emulated.

In act 88, one or more CAD tools for performing the alteration are selected. Any CAD tools may be used, such as standard or custom designed CAD tools. In one embodiment, a CAD tool defining a plane is invoked for a cutting plane. The portion to be removed is then removed using a deletion CAD tool, resulting in movement or change of the mesh to be along the plane. The script indicates the CAD tools to use and defines the operation of the CAD tools based on the alteration and location information.

In act 87, the invoked CAD tools are used to alter the surface. The mesh and/or matrices defining the surface are changed to account of the alteration. For example, a CAD cutting tool removes the pathological part of the bone based on parameters defined by the script and detected features.

For example, the script implemented by the CAD tool may be CutSurface(cuttingPlane, shiftedMostDistalPoint). The result of alteration is the current surface provided in act 72 for the next iteration of the sequence.

In act 90 and act 38, the orthopedic surgical plan for one or more bones of the patient is generated. After sequencing through the rules, a series of alterations is determined. The plan is generated from the results of sequencing.

In one embodiment, the surface resulting from the sequencing is output as the plan. The plan indicates the desired result relative to the bone or bones of the patient. A three-dimensional rendering from any view, such as user selected view, is output as the plan. Multiple planar views may alternatively or additionally be output, such as a view from each of three orthogonal axes.

Figure 5:
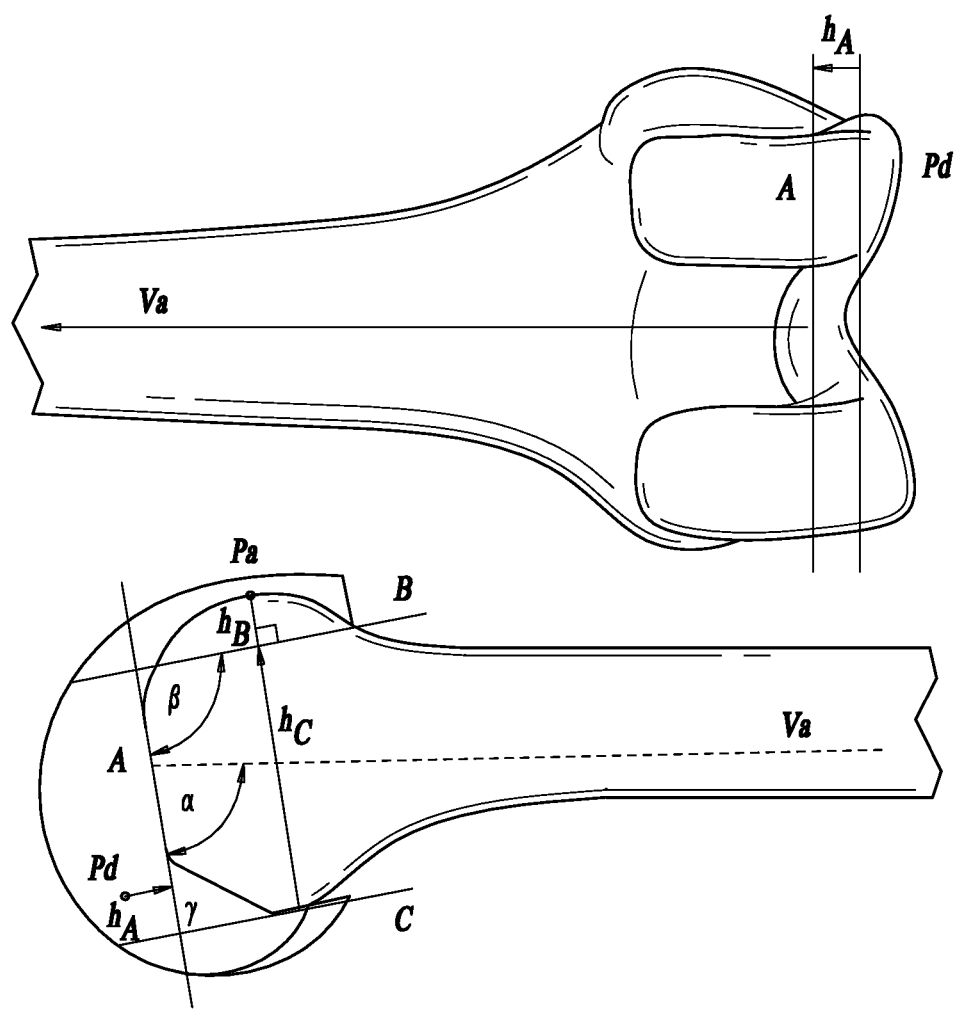
FIG. 5 illustrates an example surgical plan referenced to a femur bone.

In another embodiment, the starting bone surface with graphics indicating cutting locations or the location and type of alteration is output as the plan. The plan indicates the desired alterations relative to the starting bone or bones. FIG. 5 shows an example surgical plan for the femur bone. In the top image of the multi-planar reconstruction, reference plane A is defined on the anterior view, and planes B and C based on plane A are shown on the medial view. Reference plane A normal is defined as a vector that is generated by rotating anatomical axis $v_a$ about the medial-lateral axis by angle $\alpha$. The plane is positioned at a distance $h_A$ from the most distal point $p_d$ on the bone. Plane B is defined by rotating plane A by angle $\beta$ along the anterior-posterior axis, and positioned at a distance $h_B$ from the most anterior point $P_a$. Plane C is positioned distance $h_c$ from B, and then rotated to make an angle $\gamma$ with plane A. The output plan may be more involved.

Rather than or in addition to showing the beginning point and/or end point of the plan, various stages or steps may be shown. For example, the bone at different points in the procedure is shown. A sequence of images representing the sequence of operations is output as the plan.

In yet other embodiments, a textual summary of the alterations and parameters relative to a specific bone of a specific patient are output. A list of actions is indicated.

Combinations of text and images may be used. For example, a sequence of alterations and corresponding before and/or after images are shown. The images are of the bone surface for the particular patient.

The plan may or may not include implant information. For example, one or more images indicate a position of the implant relative to the surface after cutting. The implant placement relative to the altered bone is modeled. A representation of the implant and implant placement with the bone of the patient altered according to the rest of the plan assists the surgeon in the final acts of implanting the implant. The images assist the surgeon in placement of the implant relative to the altered surface.

Where the implant impacts multiple bones, the implant placement may be modeled relative to the different bones. For example, the rules indicate the position of the implant relative to one bone based, in part, on the orientation, shape, and/or location of features or implants on an adjacent bone. The plan may include an image showing this relative positioning of implant or implants to more than one bone.

Other implant information may be determined and output. For example, one or more rules may include operations to determine a size and/or type of implant to be used as well as implant placement. Once features are detected, the features are employed to determine the optimal size, type, and position of the implant.

In act 40 of FIG. 3, a cutting guide is automatically designed. For implementing the surgical plan, the surgeon may be assisted by a cutting guide. The cutting guide guides the location of cuts or other alterations. Slots, holes, surfaces, markings, or other structure on the cutting guide directs the alteration tools (e.g., saw or drill) and/or directs the surgeon on where to alter.

One or more alterations may be guided by the cutting guide. Less than all or all of the alterations are guided. For example, a cutting guide for the femur includes a slot for guiding the cutting of the bone along plane A, but not the other planes.

The cutting guide is specific to the patient. Since the location of features differs from patient to patient, the location of the alteration is different from patient to patient. A stock or common cutting guide may not account for these differences. Instead, the cutting guide is modeled specific to the patient. The size, shape, configuration, and/or guide locations are modeled for the specific bone surface. For example, contact surfaces or point in the cutting guide are conformed to the bone of the patient for proper positioning of the cutting planes.

The design of the cutting guide is based on the rules. The script includes rules for modeling the cutting guide. The output from processing the cutting guide design rules are not included in the surgical plan other than to indicate placement of and use of the cutting guide during surgery. Alternatively, the plan includes additional cutting guide design information.

In act 42, the size, shape, and guide location of the cutting guide are modeled. An abstract template for the cutting guide is altered to the surgery and/or bone surface of a given patient. The cutting guide is personalized to the starting surface of the bone of the patient to provide the desired final surface of the bone for implantation. The cutting guide is fit to the surface of the bone so that the cut or other alteration position is indicated on the guide for the desired alteration of the bone.

In one embodiment, the cutting guide design workflow includes using the surgical plan information for the placement of the cutting guide. For example, one constraint is the alignment of plane A relative to the cutting guide. The cutting guide template parameters are adjusted for the patient, such as determining finger length and depth based on bone surface features. Any parameters may be used, such as a surface shape, surface contact points, length, width, and/or angles. After conforming the cutting guide model to the bone surface, the data representing the bone surface is removed. The result is the designed cutting guide specific to a given patient. Once features are detected, the features are employed to design the personalized cutting guide with certain constraints based on the template and/or rules.

The cutting guide model is output to a manufacturer. The manufacturer creates the personalized cutting guide for the surgery of the patient. The model indicates a type of cutting guide and one or more values for variable parameters used in personalization. The model may indicate, through the type or through values for parameters, aspects of the cutting guide common to different patients. The template, placement relative to the bone surface, and sizing values are constraints for the design.

Where two bones are to be altered in a surgery, separate cutting guides are designed and used for the different bones. The design of the cutting guides and/or the alterations for one bone may be relative to the other bone or independent of the other bone. Similarly, the cutting guides are dependent on or independent of each other. In an alternative embodiment, one cutting guide indicates alterations for more than one bone. For example, the cutting guide is to be mounted to or placed against two bones for guiding alterations on both bones.

In additional or alternatively, the implant may be modeled and personalized. Rather the using implants by standard or available type and size, the sizing and/or shape of the implant may be modeled using the rules and the bone surface. For example, an angle of a base of the implant relative to a surface (e.g., ball) to interact with another implant is set based on the relative angle of axes of two bones. Other personalization to account for patient-to-patient variation may be used. The implant model is output for manufacture of a personalized bone implant.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

What is claimed is:

1. A method for orthopedic surgical planning, the method comprising:
    providing a knowledgebase of rules for orthopedic surgery to a bone of a patient;
    obtaining a surface representing the bone, an implant, or a cutting guide;
    selecting, by a processor, a first rule of the knowledgebase;
    identifying, by the processor, at least one anatomical feature for the first rule;
    detecting, by the processor, the at least one anatomical feature of the surface;
    defining, by the processor, an alteration to the surface as a function of the first rule and the at least one anatomical feature;
    altering, by the processor, the surface according to the alteration, resulting in a first altered surface;
    outputting, by the processor, a reference plan showing an implant and position of the implant relative to the first altered surface of the bone; and
    generating, by the processor, a cutting guide model of a physical cutting guide personalized to the bone of the patient, the cutting guide model generated as a function of the first altered surface, the cutting guide model indicating an alteration to provide the first altered surface.

2. The method of claim 1 wherein providing the knowledgebase of the rules comprises providing the rules as context free grammar in a scripting language supporting geometric primitives, wherein identifying, detecting, and defining are performed by a script interpreter, and wherein altering is performed by a surface shaping engine.

3. The method of claim 1 wherein providing the knowledgebase of the rules comprises scripting the rules for preparing the bone and another bone for the implant.

4. The method of claim 1 wherein obtaining comprises receiving segmented medical data.

5. The method of claim 1 wherein selecting the first rule comprises sequencing through the rules, each of the rules associated with acts to form the bone for the implant, the first rule being a last of the rules.

6. The method of claim 1 wherein identifying comprises indicating in the first rule the anatomical feature for positioning the alteration relative to the bone, wherein detecting comprises detecting with a feature detector, and wherein defining the alteration comprises locating the cut position based on the at least one anatomical feature and indicating a portion of the bone removed relative to the cut position.

7. The method of claim 1 wherein altering comprises implementing a computer assisted design tool.

8. The method of claim 1 wherein altering comprises emulating removal of a portion of the bone.

9. The method of claim 1 wherein outputting comprises outputting the reference plan with an implant size, an implant type, and implant placement.

10. The method of claim 1 wherein generating the cutting guide model comprises fitting the cutting guide model to the surface, positioning the cut position relative to the fitted cutting guide model, and indicating a guide on the cutting guide model for the cut position.

11. The method of claim 1 further comprising performing the selecting, identifying, detecting, defining, and altering for a second rule prior to the first rule, the surface being defined by the performing for the second rule.

12. The method of claim 1 wherein outputting comprises outputting the reference plan based on, at least in part, patient bone information comprising bone size, shape, and density.

13. In a non-transitory computer readable storage medium having stored therein data representing instructions executable by a programmed processor for orthopedic surgical planning, the storage medium comprising instructions for:

sequencing through work instructions representing alterations of geometry based on anatomical features;

generating an orthopedic surgical plan for a patient in response to the sequencing;

modeling the implant and placement of the implant relative to the bone of the patient; and generating a cutting guide manufacture design for manufacture of a patient specific cutting guide configured for the bone of the patient.

14. The non-transitory computer readable storage medium of claim 13 wherein sequencing comprises interpreting script for the work instructions of a knowledgebase.

15. The non-transitory computer readable storage medium of claim 13 wherein generating an orthopedic surgical plan comprises indicating a sequence of alterations of the bone for the implant placement, an implant size, and an implant type.

16. The non-transitory computer readable storage medium of claim 13 wherein modeling comprises outputting a representation of the placement of the implant with the bone of the patient altered according to the orthopedic surgical plan.

17. The non-transitory computer readable storage medium of claim 13 wherein generating the cutting guide manufacture design comprises determining a size, shape, position, and guide location for a cutting guide specific to the bone of the patient.

18. The non-transitory computer readable storage medium of claim 13 wherein generating an orthopedic surgical plan comprises generating the surgical plan for the bone and an additional bone of the patient, wherein modeling comprises modeling the placement of the implant relative to the bone and the additional bone, and wherein generating the cutting guide manufacture design comprises designing a cutting guide for the bone and an additional cutting guide for the additional bone.

* * * * *